United States Patent
Lee

(10) Patent No.: US 8,852,129 B2
(45) Date of Patent: Oct. 7, 2014

(54) STROKE REHABILITATION PROGRAM

(76) Inventor: Michael E. Lee, Eugene, OR (US)

( * ) Notice: Subject to any disclaimer, the term of this patent is extended or adjusted under 35 U.S.C. 154(b) by 1078 days.

(21) Appl. No.: 12/380,675

(22) Filed: Mar. 2, 2009

(65) Prior Publication Data

US 2009/0270768 A1   Oct. 29, 2009

Related U.S. Application Data

(60) Provisional application No. 61/125,575, filed on Apr. 26, 2008.

(51) Int. Cl.
- *A61B 5/117* (2006.01)
- *A61B 5/103* (2006.01)
- *A61B 5/11* (2006.01)
- *A61B 5/00* (2006.01)

(52) U.S. Cl.
CPC .............. *A61B 5/1124* (2013.01); *A61B 5/1101* (2013.01); *A61B 2505/09* (2013.01); *A61B 5/486* (2013.01); *A61B 5/6806* (2013.01)
USPC ........................................................ 600/595

(58) Field of Classification Search
USPC ...................... 600/595, 587, 300, 529; 601/24
See application file for complete search history.

(56) References Cited

U.S. PATENT DOCUMENTS

2005/0027207 A1* 2/2005 Westbrook et al. ............ 600/529
2006/0287617 A1* 12/2006 Taub et al. ...................... 601/24

OTHER PUBLICATIONS

Gaggioli et al, Training with Computer-Supported Motor Imagery in Post-Stroke Rehabilitation, CyberPsychology & Behavior, vol. 7, No. 3, 2004, pp. 327-332.*
Gaggioli et al, A Strategy for Computer-Assisted Mental Practice in Stroke Rehabilitation, Neurorehabil Neural Repair 2006, 20:503-507.*
"Nanotechnology Brings Brain Recovery in Sight." Nanotechnology, Mar. 14, 2006, MIT, May 26, 2009, <http://www.physorg.com/print11755.html>.
"Telemedicine Leads to Better Stroke Treatment Decisions." California Institute for Telecommunications and Information Technology, May 26, 2009, <http://www.calit2.net/newsroom/print_page.php?id=1345>.

* cited by examiner

*Primary Examiner* — Brian Szmal
(74) *Attorney, Agent, or Firm* — Alleman Hall McCoy Russell & Tuttle LLP

(57) ABSTRACT

A method for the treatment of paralysis caused by injury to the brain. A set of movements by a healthy extremity is recorded and stored in a computer. Movements made by an affected extremity are recorded and compared to the standard provided by the healthy extremity. A score based on the similarity of the movement is reported to the user to aid in tracking progress. A similar system may also be used to detect and track the progress of degenerative diseases by comparing past movements to current movements.

51 Claims, 4 Drawing Sheets

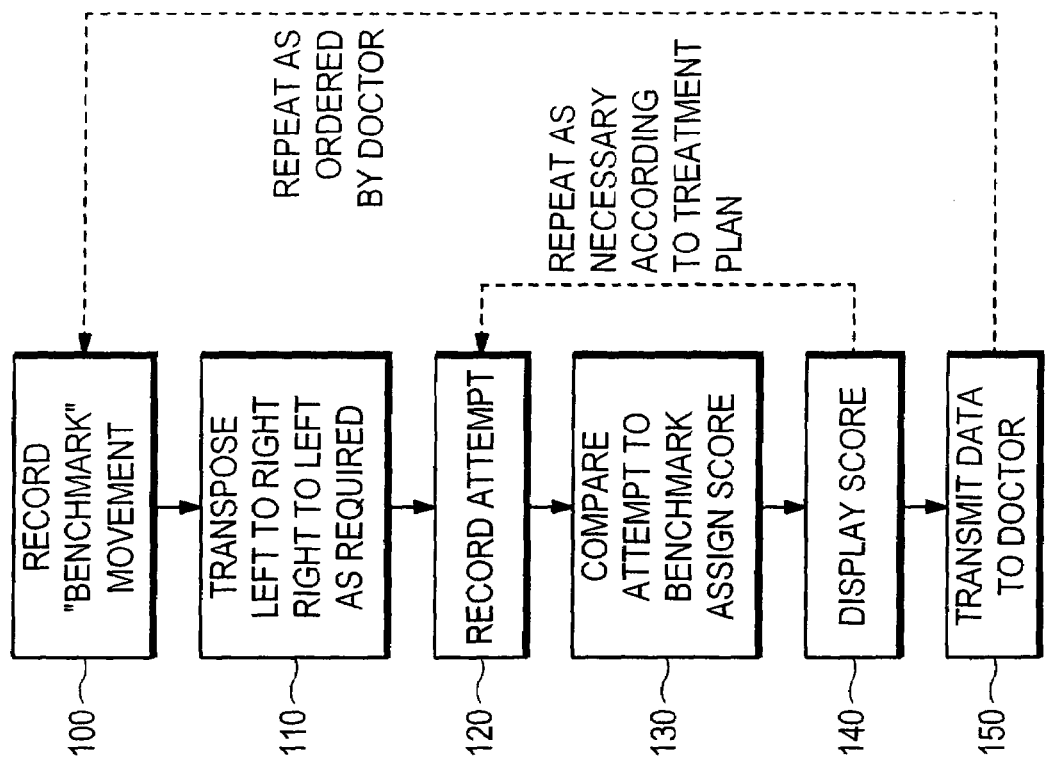
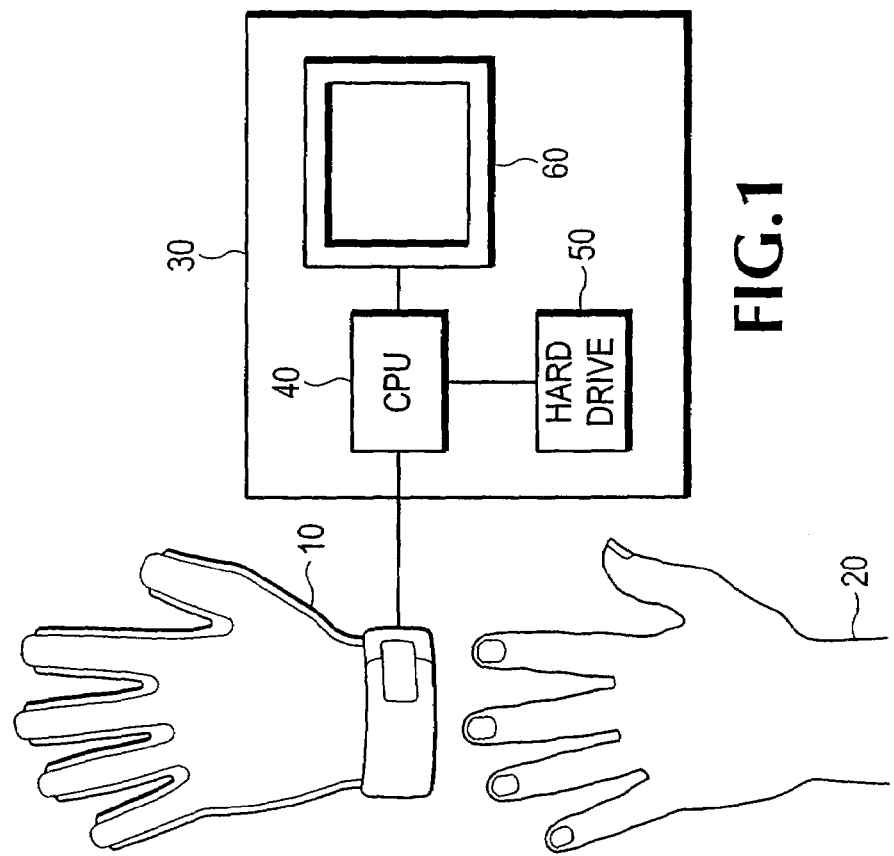

STROKE REHABILITATION PROGRAM

CROSS REFERENCE TO RELATED DOCUMENTS

The present application claims the benefit of Provisional Pat. App. No. 61/125,575, filed Apr. 26, 2008.

BACKGROUND OF THE INVENTION

The present invention relates to physical and neurological rehabilitation of, in many cases, victims of brain damage and stroke, and in particular the repetitive therapy necessary to regain function.

Victims of brain injury, including injury caused by stroke, often find themselves paralyzed or with severely limited mobility despite having healthy muscles and bones. This is the result of damage to brain tissue and neurons responsible for controlling the affected muscles. It has long been believed that this kind of nerve injury was essentially irreversible. However, modern research has shown that human nerve cells and brain material is much more plastic than previously thought, and that nerves and brain cells can grow and strengthen in response to exercise just as muscles and bones do. This insight gives hope that victims of brain injury may be able to regain function lost through the injury by intensive therapy. The therapy tends to involve massive repetition of the injured part of the body.

The therapy required for nerve growth and healing is intensely repetitive and requires consistent daily practice over a long period of time to show readily observable results. The typical therapy to regain function in a injured limb involves placing a mitt over the non-affected limb. Then one attempts to train the affected side by repetitively repeating selected tasks. Unfortunately, the physical therapist often cannot detect minor progress made with extended effort, and progress over time generally goes unnoticed. Thus it is difficult for the physical therapist to measure how well the activity is performed, especially with minor differences in how the activity is perceived. After a limited time with the physical therapist, the patient is sent home to continue to practice.

It is too expensive for most patients to conduct repeated sessions with the assistance of professionals, such as physical therapists. Unless a patient is wealthy enough to hire a therapist to help, the majority of therapy must be conducted on the initiative of the patient, usually at the patient's residence. But because therapy is boring and progress slow, most patients lose motivation before they achieve sufficient progress to make the affected limb really useful again. Then, because the affected limb is not useful, it tends to not be used. Thus, other ways of accomplishing daily tasks are found. Muscles atrophy with non-use, and nerves in like fashion gradually lose their ability to stimulate muscles. Through this process of "learned nonuse," the injury becomes permanent and irreversible.

What is needed, then, is a method for conducting therapy of brain-injured patients which is cost effective and that will enable patients to maintain their motivation by watching and being rewarded by incremental progress towards their recuperative goals.

BRIEF SUMMARY OF THE INVENTION

In one embodiment, the movement of an extremity relatively unaffected by the brain injury to the affected hemisphere is recorded to establish a "benchmark" of desired movement to which the affected limb may subsequently be compared. Preferably this benchmarking limb is found on the patient himself, but it may also be the limb of another person. The recording may be accomplished by any known technique, and preferably allows for easy digitization and storage in a retrievable storage medium, for example the hard drive of a computer. For instance, the "CyberGlove" from Immersion Corporation is fitted with sensors to capture the movement of the wrist and fingers in digital format. Several iterations of a given movement may be recorded so that the "average" movement and acceptable deviations therefrom may be computed and small measurement errors minimized.

Once recorded, the benchmark movement serves as a basis for comparison with movements undertaken by the affected extremity. It may be digitally transposed (from right to left handedness or left to right handedness) if necessary to facilitate comparison between the two. Attempts to duplicate the benchmark movement on the affected limb are then recorded in the same fashion as the benchmark movement. The benchmark and an attempt are compared. Preferably, this comparison is carried out automatically by a computer. The attempt is then scored based on how closely it matches the benchmark, and the results are provided to the patient. The results may be presented in graphical fashion. Using a graphical display, together with feedback, is generally quite addictive for therapy when presented in the form of a game.

Attempts or their scores may also be recorded in order to track changes in ability over time. The patient's scores may be periodically transmitted to a medical professional, such as a physician or physical therapist, for review and, if necessary, adjustment, using a telecommunications network, for example, the Internet. Complete data, including the details of each attempt, may also be transmitted to enable the professional to identify specific issues which merit attention.

A similar technique may be used to monitor a patient for onset or progression of other diseases. For instance, some degenerative brain diseases cause the hands to tremble. After recording of a benchmark performance of ordinary tasks, the patient may periodically perform those same tasks so that any tremors or other signs of disease may be detected at an early stage. The comparison between benchmark and later attempts could be performed automatically by computer or could rely on transmission of the data to a medical professional for evaluation.

The foregoing and other objectives, features, and advantages of the invention will be more readily understood upon consideration of the following detailed description of the invention, taken in conjunction with the accompanying drawings.

BRIEF DESCRIPTION OF THE SEVERAL VIEWS OF THE DRAWINGS

FIG. 1 is a schematic showing an apparatus which may be used to implement the claimed methods.

FIG. 2 is a flowchart showing the steps used in an embodiment to treat an injured patient.

DETAILED DESCRIPTION OF PREFERRED EMBODIMENT

Figure 4:
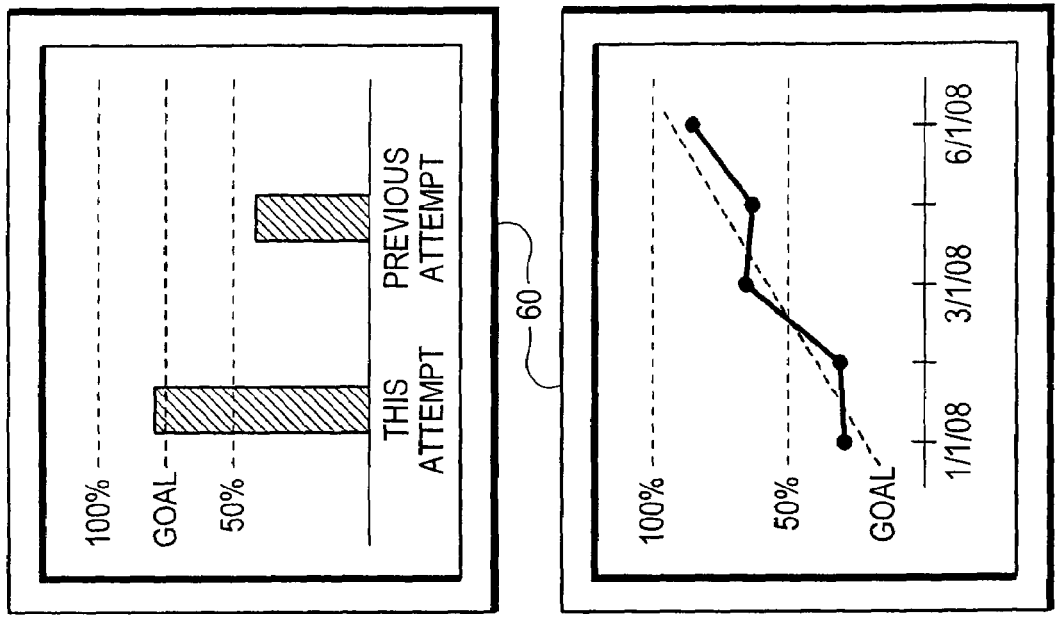
FIG. 4 shows several embodiments of a display.

Turning now to the attached drawings, FIG. 1 depicts one possible apparatus for use in implementing the technique. Following the steps outlined in FIG. 2, the technique may be implemented as follows to assist a patient who has lost function in one hand due to brain injury. The typical brain injury is hemiplegic stroke, although the techniques described herein may be used for other types of injuries.

A first glove 10 fitted with digital sensors, such as the "CyberGlove" from Immersion Technologies, is placed over a healthy hand 20 of a patient. The glove is connected to a digital recording apparatus such as a computer 30, for example by USB cable. In the first step 100 of the process, the patient performs a series of movements designed by a physical therapist or physician to maximize recovery. These movements are recorded by the computer and stored in a durable form, such as on hard drive 50. The movements may be performed several times to allow for averaging or other statistical measure. These recorded movements form the "benchmark" towards which the recovering patient will strive. The benchmark movements may also be performed by a person other than the patient, for example, a physical therapist. It may be necessary for the therapist to do so if the patient has lost function in both hands. Preferably, these benchmark movements are performed in cooperation with the physical therapist and/or treating physician so that an accurate set of benchmark movements are determined. Moreover, there may be multiple different benchmark movements, each of which is for a different exercise.

In the second step 110, the recorded "benchmark" movements may be digitally transposed by a processing unit, such as the CPU 40 of the computer 30, and re-recorded on the hard drive 50. This transposition "reflects" the movements in a mirror-like fashion so that direct comparisons between the benchmark movements and the injured hand are possible. Alternatively, the transposition may be performed on the later movements by the injured hand, or a comparison algorithm designed for comparing non-transposed data might be used. In the event that the "benchmark" movements are made by someone other than the patient, they may not require transposition at all. As a general matter, the intra-hemispheric training technique results in benchmarks which include generally graceful movements that may subsequently be used as the basis for training the injured hand.

In the third step 120, a second glove 10 (or the same glove) is fitted over the hand 20 which is to be treated. The patient then attempts to perform the same movements previously performed with the healthy hand. The computer again may record the movements on the hard disk.

In the fourth step 130, the movements by the hand to be treated are compared to the benchmarks, and a score is assigned based on how closely the patient has managed to duplicate the baseline movement the score may be any type of indication of how the patient did. Preferably, this scoring is accomplished by the computer 30, but could be done by a person. The score may be recorded on the hard drive 50 or stored in any other manner.

In the fifth step 140, the score is outputted to the patient, for example by displaying it on the monitor 60. This display may show, for instance, a numerical score. It may also use graphical displays, such as graphs or charts, to display the score, such as, for example, as shown in FIG. 4. The scoring display may include past scores, for example in bar- or line-graph format, to track progress over time.

Steps 3-5 may be repeated many times during a single therapy session or over the course of multiple therapy sessions, which may occur over the period of weeks or months as prescribed by the treating physician or other medical professional. The therapy sessions may be performed with the physical therapist or by the patient on their own. The capability to have effective therapy from home or another convenient place also lowers the expense associated with going to the physical therapist.

By providing nearly immediate or otherwise timely feedback by using the computer system, the patient can observe their progress. The computer system can likewise track the patients progress over time, and therefore the patient also receives on-going feedback. By performing exercises and receiving continual feedback, the system becomes generally addictive to the patients. With the addictive nature of the computer feedback system, the patient is considerably more likely to perform the exercises on a regular and on-going basis. In addition, the computer system and feedback can show minor improvements in the technique. Typically, the minor improvements would have otherwise not been observable, so this provides further incentive for the patient to do the exercises on a regular basis. This feedback is useful for encouraging long-term recovery, which tends to be facilitated by extensive repetition of exercises.

In the sixth step 150, the recorded information may be transmitted to a medical professional for evaluation. This step, while optional, is relatively inexpensive and it may be useful to assist a patient's doctor or therapist in evaluating progress or altering the therapy regime to improve recovery. The professional may be a medical doctor, nurse, physical therapists, chiropractor, neurologist, personal trainer, physiatriast, or any other person responsible for monitoring and/or caring for the patient. The transmitted information may consist only of scores, or it may consist of the detailed recordings of the movements, or both. The transmission may occur over a telecommunications network, including the Internet, LAN/WAN, phone lines, and satellites, or directly by radio signals, for example Wi-Fi. It may also occur by movement of tangible records, for example paper printouts or digital data stored on a floppy disk, magnetic tape, CD, or other storage medium, and sent by U.S. Mail, bicycle courier, United Parcel Service or any other similar delivery service. The person evaluating the progress of therapy may suggest that the patient begin again at step 1 with new and perhaps more challenging movements.

Based upon the received information, the medical professionals may provide feedback to the patient in their progress. Also, based upon the received information, the medical professionals may modify the therapy performed by the patient. In this manner, the medical professionals may view the progress of the patient, the frequency of the exercises, the duration of the exercises, and otherwise monitor the progress of the patient. Moreover, the medical professional may provide feedback in a very efficient and cost effective manner. Similarly, the patient doing missed practices of interhemispheric teaching at home being inspired by even a small amount of progress, normally not observable by even the best therapists.

A similar technique may be used to treat other portions of a patient's body, such as the arm, shoulder, foot, or leg, provided that a suitable device for detecting the movement of the treated extremity were employed in place of the glove 10.

Figure 3:
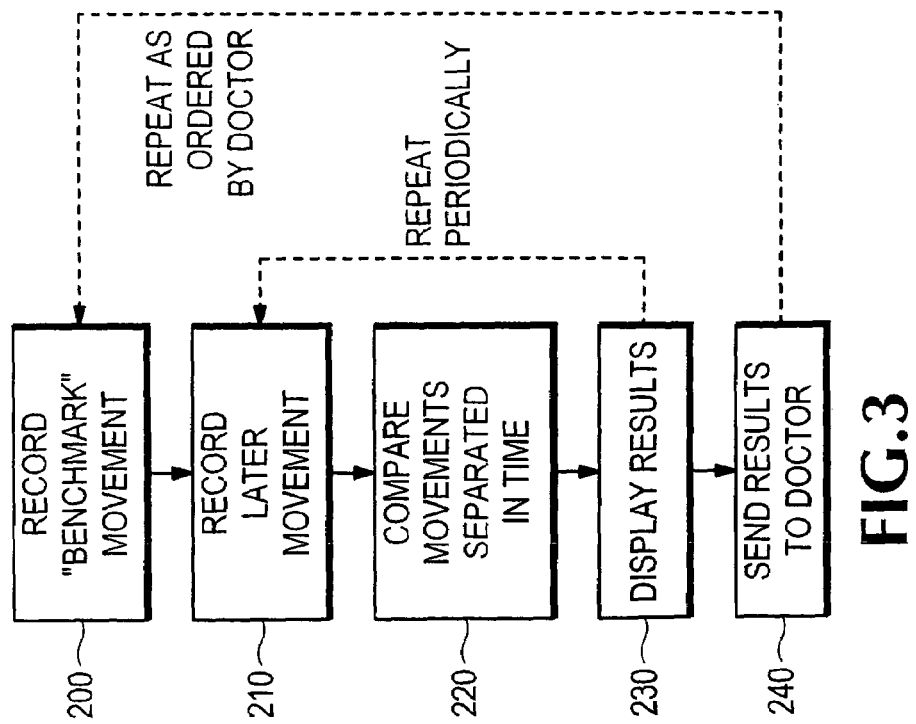
FIG. 3 is a flowchart showing the steps used in an embodiment to detect and monitor a degenerative disease.

A similar set of steps using the same apparatus may be used to monitor patients for the onset or progress of a disease which affects movement, as show in FIG. 3.

In the first step 200, baseline movements are recorded and stored using the glove 10 and computer 30. These movements may be designed by a medical professional to facilitate diagnosis, or they may be ordinary and everyday movements.

In the second step 210, the movements are repeated at a later time and recorded and stored by the computer 30.

In the third step 220, movements taken at different times are compared and analyzed for signs of disease, for example, reduced coordination or involuntary tremors, and the results of the analysis are stored.

In the fourth step 230, the results are outputted, for example by displaying them on the monitor 60. This output may include a display of multiple past results to show a progression over time.

Steps 2-4 may be repeated as often as necessary for monitoring purposes. They may occur at regular intervals or in response to specific events.

In the fifth step 240, the data and results may be transmitted to a medical professional for evaluation by any method. The patient may be instructed to repeat starting at the first step if necessary using alternative movements.

The rehabilitation of the patient can also be the basis of a providing medical diagnosis in order to determine brain activity. While doing rehabilitation activity, a brain scanning device can observe portions of the brain. Based upon those portions of the brain that are operational, or otherwise not operational, a trellis may be implanted within the brain in order to provide a physical structure for repairing the brain. The trellis structure may be used in conjunction with nano-technology to have a self-construction device. As the brain builds on the trellis structure, the brain may operate better.

A nano-technology based implant material may likewise be used to insert into the brain in those locations that are not fully operational. Based upon readings of a brain scanning device, the system may determine the type of nano-technology device, the type of material, and the optimal location for that type of device/material. This material may be used in conjunction with the trellis or separate from the trellis.

Another embodiment may use a modified virtual therapy team process where the patient has a computer software program for assistance. Even with the software running on a computer and the training device, the patient is still at home alone. Being alone makes it difficult to maintain motivation to do the necessary exercises, even with near immediate feedback on performance. Sometimes the necessary practice takes 6-8 hours a day for increased effectiveness. It is desirable to include all of the team members in the "at home" environment by using the power of interconnected computers. One or more of the team members for the interhemispheric rehabilitation process can each have their own computer program, each at remote locations from one another, while collectively working toward the common treatment of the patient. Thus, the patient does not feel they are alone in their rehabilitation process, although they may still be at home alone. The team members may observe the progress and provide comments/feedback to all members of the team.

Figure 5:
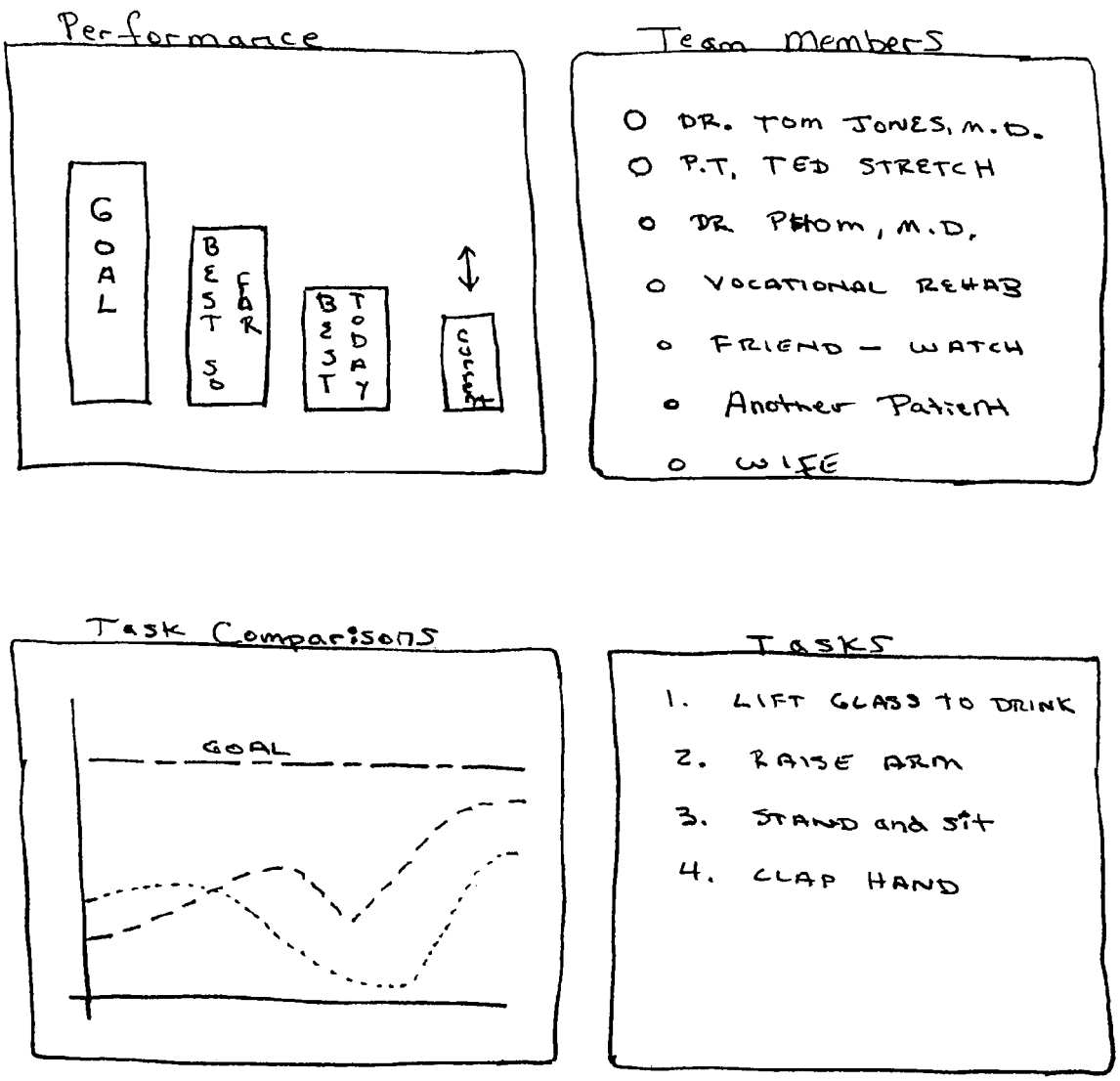
FIG. 5 illustrates graphical presentation of information.

Referring to FIG. 5, when a team member logs into the system, they may view a graphical display. The display may include performance measures. One measure may be the goal. Another measure may be the particular patient's best so far. One measurement may be the particular patient's best today. Yet another measurement may be the patient's current performance which may be a dynamically changing graph. The display may also include a listing of the team members. The team members that are currently logged into the system may be identified. Showing logged in team members facilitates the ability for team members to initiate contact with one another, either through computer communication (messaging, e-mail, etc.) or a telephone call. The display may also illustrate a comparison between different tasks. The tasks may likewise be shown relative to a benchmark goal. This graph may be used to provide feedback and observe progress. The display may also illustrate a set of tasks for the patient and/or other team members. The team members may modify the tasks. The user may elect to archive the data, if desired.

With the virtual interactive team, the feedback from its members may relate to actual interhemispheric progress. Also, the feedback may be provided often in a very cost effective manner, thus increasing the quality of healthcare while simultaneously reducing its costs.

Figure 6:
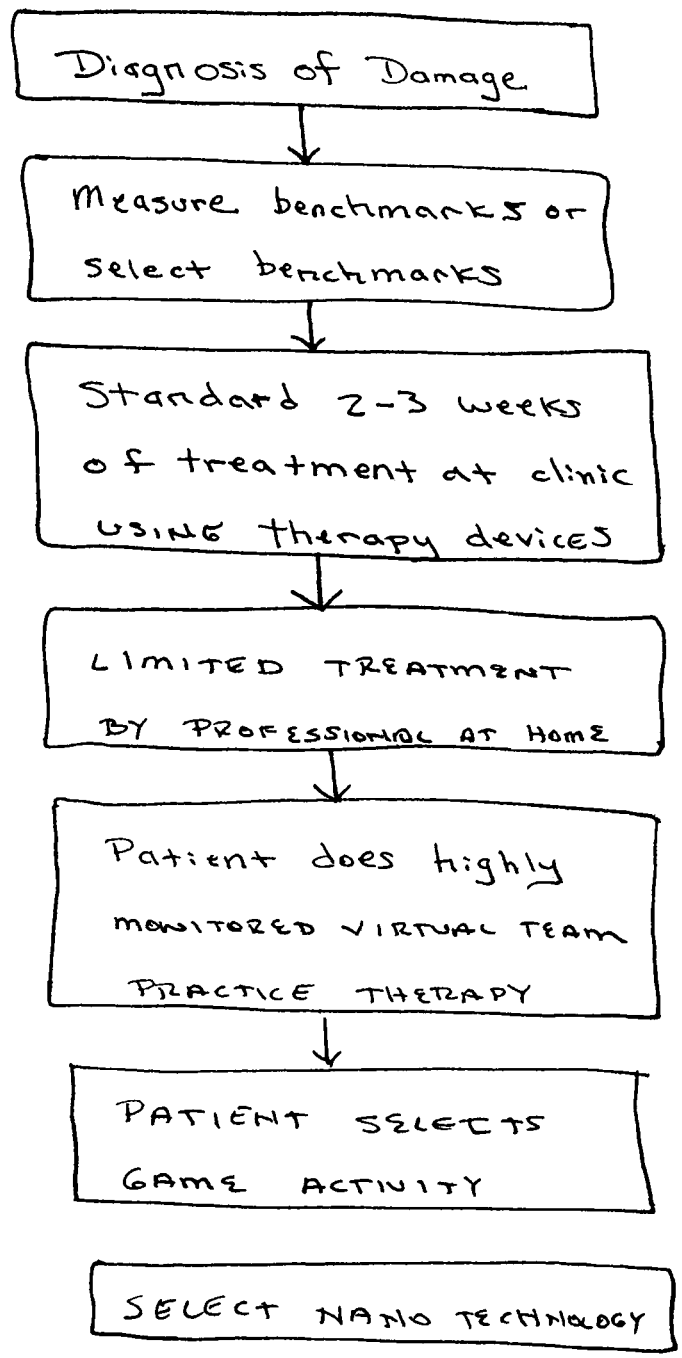
FIG. 6 illustrates a diagnostic technique.

Referring to FIG. 6, one technique to achieve rehabilitation is to first diagnosis the type and extent of the damage. Based upon this initial assessment, a set of tests may be selected from which benchmark tests are obtained from the patient. In some cases, a set of pre-stored benchmarks may be selected. This provides a standard to measure the treatment relative to the benchmark. The patient may spend 2-3 weeks at a clinic receiving treatment. Preferably, the computer system is used so that good feedback is provided. This also allows the patient to become familiar with the computer system. After treatment at the clinic, the patient goes home and continues treatment with the benefit of a professional. After this initial treatment, the patient continues with extensive therapy using the therapy devices and computer system. The team members may provide assistance to encourage, monitor, and direct the rehabilitation. Different tasks may be selected by the patient and/or from multiple different activities. Based upon this treatment, a nano-technology may be selected, if desired.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed:

1. A method of rehabilitating injured patients of hemiplegic injury, comprising:
    (a) providing a rehabilitation practice task, including:
        (i) recording movements with motion capture sensors made by a first part of a body of a patient less or not affected by said hemiplegic injury to establish a benchmark of recorded movements captured with the motion capture sensors, wherein said motion capture sensors are placed on said first part of said body of said patient;
        (ii) recording movements with the motion capture sensors made by a second injured part of the body affected by said hemiplegic injury, where the movements are intended to imitate said movements made by said first part of the body;
        (iii) comparing said movements by said second part of the body to said benchmark of said first part of the body and assigning and displaying a current score based on their similarity;
        (iv) outputting real-time feedback, to said patient at home, based on said score to said patient and dynamically displaying the current score relative to a goal based on the benchmark to show minor improvements, where the minor improvements are otherwise not visually observable; and
        (v) repeating steps (ii), (iii) and (iv) by said patient in an attempt to improve said score so as to rehabilitate the effects of said hemiplegic injury.

2. The method of claim 1 wherein said first part of the body and said second part of the body are located on the same individual.

3. The method of claim 2 further comprising the step of digitally transposing the movements of one of said parts of the body in a mirror-image fashion where the recorded benchmark movements are digitally transposed for comparison of the benchmark recordings and the recorded movement of the injured part of the body.

4. The method of claim 1 further comprising the step of displaying said score in a graphical fashion.

5. The method of claim 1 further comprising the step of storing said current score in a non-transitory storage medium.

6. The method of claim 5 further comprising the step of displaying past scores together with said current score.

7. The method of claim 6 further comprising the step of displaying said past scores and said current score in a graphical fashion.

8. The method of claim 6 further comprising the step of sending said past scores to a medical professional.

9. The method of claim 1, further comprising:
   providing feedback from a virtual therapy team process, including:
   (i) transmitting said score via a telecommunications network to interconnected computers of team members of a virtual interactive team wherein at least two of the team members are in remote locations from each other;
   (ii) receiving feedback from said team members over said telecommunications network; and
   (iii) repeating steps (i) and (ii) in an attempt to improve said score so as to rehabilitate the affects of said hemiplegic injury.

10. The method of claim 1 wherein said recording is accomplished in digital format.

11. The method of claim 1 wherein said second part of the body is affected by an injury, but said first part of the body is unaffected by said injury.

12. A method of rehabilitating injured patients, comprising:
   (a) recording movements with motion capture sensors made by a first part of a body of a patient to establish a motion capture benchmark, wherein said motion capture sensors are placed on said first part of said body of said patient;
   (b) recording movements with motion capture sensors made by a second part of the body intended to imitate said movements made by said first part of the body;
   (c) comparing said movements by said second part of the body to said benchmark of said first part of the body and assigning a current score based on their similarity; and
   (d) outputting said current score to the patient and a virtual therapy team through an interconnected telecommunications network, wherein the virtual therapy team comprises at least two team members in remote locations from each other and wherein at least one team member is a non-medical professional; and
   (e) receiving feedback from the virtual therapy team to the patient through the telecommunications network to the patient.

13. The method of claim 12 wherein said first part of the body and said second part of the body are located on the same individual.

14. The method of claim 13 further comprising the step of digitally transposing the movements of one of said parts of the body in a mirror-image fashion.

15. The method of claim 12 further comprising the step of displaying said score in a graphical fashion.

16. The method of claim 12 further comprising the step of storing said current score in a non-transitory storage medium.

17. The method of claim 16 further comprising the step of displaying past scores together with said current score.

18. The method of claim 17 further comprising the step of displaying said past scores and said current score in a graphical fashion.

19. The method of claim 12, further comprising the step of listing and displaying the virtual team members to facilitate team communication.

20. The method of claim 12, wherein the current score is an indicator of minor improvements from the motion capture benchmark wherein the minor improvements are otherwise not observable.

21. The method of claim 20, wherein the displaying of the current score includes displaying a graphical comparison between the motion capture benchmark and the current score.

22. The method of claim 12 wherein the virtual therapy team further includes at least one medical professional.

23. A method of rehabilitating injured patients of hemiplegic stroke, comprising:
   (a) recording movements with motion capture sensors made by a first part of a body of a patient to establish a motion capture benchmark, wherein said motion capture sensors are attached to the patient;
   (b) recording movements with motion capture sensors made by a second part of the body intended to imitate said movements made by said first part of the body;
   (c) comparing said movements by said second part of the body to said movements made by said motion capture benchmark of said first part of the body and assigning a current score based on their similarity;
   (d) outputting said current score through an interconnected computer network through a virtual therapy team process, wherein the virtual team process includes display of performance measures to a virtual team on the interconnected computer network, where the virtual team includes at least one non-medical professional and one medical professional and where at least two members of the virtual team are at remote locations from one another.

24. The method of claim 23 wherein said first part of the body and said second part of the body are located on the same individual.

25. The method of claim 24 further comprising the step of digitally transposing the movements of one of said parts of the body in a mirror-image fashion.

26. The method of claim 23 further comprising the step of displaying said score in a graphical fashion.

27. The method of claim 23 further comprising the step of storing said current score in a non-transitory storage medium.

28. The method of claim 27 further comprising the step of displaying past scores together with said current score.

29. The method of claim 28 further comprising the step of displaying said past scores and said current score in a graphical fashion.

30. The method of claim 23 wherein the current score is displayed in a dynamically changing graph.

31. The method of claim 23 wherein the performance measures include one or more of a patient goal, patient's best so far, patient's best today and patient's current score.

32. The method of claim 23 further comprising linking and displaying of the virtual team members.

33. The method of claim 23 wherein said second part of the body is affected by an injury, but said first part of the body is less or not affected by said injury.

34. A method of rehabilitating injured patients of brain injury, comprising:
   (a) determining an at home performance measurement of a second limb of a body including:

(i) recording movements with motion capture sensors made by a first limb of a body of a patient not or less affected by said injury to establish a motion capture digital benchmark, wherein the motion capture sensors are placed on said first limb of said body of said patient;

(ii) recording movements with motion capture sensors made by said second limb of the body more affected by said injury intended to imitate said movements made by said first limb of the body;

(iii) comparing said movements by said second limb of the body to said benchmark of said first limb of the body and assigning a current score based on their similarity;

(iv) outputting feedback based on said score to a patient as the at home performance measurement; and (v) repeating steps (ii), (iii) and (iv) by said patient in an attempt to improve said score so as to rehabilitate the effects of said brain injury; and (b) using a virtual therapy team process to improve the movements of said second limb of the body, including:

(i) displaying performance measures, including the at home performance measurement, via a telecommunications network to interconnected computers of team members in remote locations;

(ii) displaying a list of currently logged in team members to said team members;

(iii) facilitating communication among said team members via said telecommunications network;

(ix) displaying feedback based on said performance measures from said team members over said telecommunications network.

35. The method of claim 34, wherein said first limb of the body and said second limb of the body are located on the same individual.

36. The method of claim 34, further comprising running a computer game for rehabilitating hemiplegic stroke based on patient attempts to match the motion capture digital benchmark.

37. The method of claim 34, wherein said injury is one of hemiplegic damage or traumatic damage.

38. The method of claim 34 wherein said performance measures further include one or more of benchmarks, goals, best so far, best today, current performance and comparisons among different tasks.

39. The method of claim 34, further comprising in the virtual team process displaying a list of tasks to said team members and receiving selection of a task from the patient.

40. The method of claim 34, wherein the performance measures are displayed in a graphical form.

41. The method of claim 34, wherein the team members include at least one non-medical professional.

42. The method of claim 41, wherein the team members further include at least one medical professional.

43. The method of claim 34, wherein at least one team member is another patient.

44. A method of rehabilitating injured patients of hemiplegic brain damage, comprising:

(a) recording movements with motion capture sensors made by a first part of a body of a patient to establish a motion capture benchmark and digitizing and transposing the movements for comparison with movement from a second part of the body, wherein said motion capture sensors are attached to the patient;

(b) recording movements with motion capture sensors made by said second part of the body intended to imitate said movements made by said first part of the body;

(c) comparing said movements by said second part of the body to said movements of said first part of the body and assigning a current score based on their similarity;

(d) outputting said current score and the motion capture benchmark to said patient at home as a dynamic visual display where the dynamic display includes a graphical display of improvements from a goal based on the motion capture benchmark where the improvements are based on attempt of the duplication of a baseline movement from the motion capture benchmark and where the improvements are minor improvements not otherwise observable other than through digital comparison to the motion capture benchmark.

45. The method of claim 44, further comprising outputting the current score and benchmark via an interconnected computer network through a virtual therapy team process, wherein the virtual team process includes display of performance measures to a virtual team on the interconnected computer network, where the virtual team includes at least one non-medical professional and one medical professional and where at least two members of the virtual team are at remote locations from one another.

46. The method of claim 45, wherein the dynamic display is a histogram.

47. The method of claim 45, wherein the dynamic display is a dynamic graph.

48. The method of claim 45, wherein outputting the current score includes displaying a graphical representation of past scores to track progress over time.

49. The method of claim 45, wherein recording movements with said sensors made by the second part of the body is limited to movements of the patient based only on viewing of the dynamic display.

50. The method of claim 45 further displaying performance measures comprising of one or more of a patient goal, patient's best so far, patient's best today, and patient's current score.

51. The method of claim 45 further comprising display of the virtual team members and communicatively linking the virtual team members.

\* \* \* \* \*